United States Patent
Sait M A et al.

(10) Patent No.: US 11,112,400 B2
(45) Date of Patent: Sep. 7, 2021

(54) BLOOD CHARACTERISTIC MEASUREMENT

(71) Applicant: HEWLETT-PACKARD DEVELOPMENT COMPANY, L.P., Houston, TX (US)

(72) Inventors: Shameed Sait M A, Bangalore (IN); Rachel M. White, Corvallis, OR (US); Chantelle Domingue, Corvallis, OR (US); Manish Giri, Corvallis, OR (US)

(73) Assignee: Hewlett-Packard Development Company, L.P., Spring, TX (US)

(*) Notice: Subject to any disclaimer, the term of this patent is extended or adjusted under 35 U.S.C. 154(b) by 155 days.

(21) Appl. No.: 15/749,116

(22) PCT Filed: Mar. 7, 2016

(86) PCT No.: PCT/US2016/021219
§ 371 (c)(1),
(2) Date: Jan. 30, 2018

(87) PCT Pub. No.: WO2017/123266
PCT Pub. Date: Jul. 20, 2017

(65) Prior Publication Data
US 2018/0224425 A1 Aug. 9, 2018

(30) Foreign Application Priority Data
Jan. 16, 2016 (IN) .............................. 201641001634

(51) Int. Cl.
*G01N 33/49* (2006.01)
*G01N 27/02* (2006.01)
(Continued)

(52) U.S. Cl.
CPC ........... *G01N 33/4915* (2013.01); *C12Q 1/56* (2013.01); *G01N 27/02* (2013.01); *G01N 33/49* (2013.01); *G01N 33/561* (2013.01); *G01N 33/86* (2013.01)

(58) Field of Classification Search
CPC .. G01N 33/4915; G01N 33/86; G01N 33/561; G01N 33/49; G01N 27/02; C12Q 1/56
See application file for complete search history.

(56) References Cited

U.S. PATENT DOCUMENTS 4,303,887 A * 12/1981 Hill ..................... G01R 27/22
324/441
6,046,051 A 4/2000 Jina
(Continued)

FOREIGN PATENT DOCUMENTS

IN 474/CHE/2015 8/2016
TW 201439530 A 10/2014
(Continued)

OTHER PUBLICATIONS

Medgadget, "Blood Coagulation Testing Using Smartphone Touch-screens," Mar. 18, 2014, 11 p.); (Web Page), http://www.medgadget.com/2014/03/blood-coagulation-testing-using-smartphone-touchscreens.html>.
(Continued)

*Primary Examiner* — Lore R Jarrett
(74) *Attorney, Agent, or Firm* — Fabian VanCott

(57) ABSTRACT

Examples herein provide a method. The method includes applying an electrical potential difference over a blood sample in a testing cassette of a microfluidic device, the cassette including a microfluidic channel through which the blood sample flows. The method includes measuring, over a duration of time, an electrical signal passing through the blood sample as the blood sample flows from a first end and coagulates at a second end of the microfluidic channel to
(Continued)

obtain a measurement function as a function of time. The method also includes correlating the measurement function to a characteristic of the blood sample.

20 Claims, 9 Drawing Sheets

(51) Int. Cl.
*G01N 33/561* (2006.01)
*C12Q 1/56* (2006.01)
*G01N 33/86* (2006.01)

(56) References Cited

U.S. PATENT DOCUMENTS

| | | | |
|---|---|---|---|
| 6,448,024 B1* | 9/2002 | Bruegger | G01N 33/86 |
| | | | 435/13 |
| 7,021,122 B1 | 4/2006 | Rosemberg et al. | |
| 7,291,310 B2 | 11/2007 | Martin et al. | |
| 2003/0148530 A1* | 8/2003 | Lauks | G01N 33/49 |
| | | | 702/23 |
| 2004/0072357 A1* | 4/2004 | Stiene | A61B 5/14514 |
| | | | 324/449 |
| 2006/0035298 A1* | 2/2006 | Hill | G01N 33/4905 |
| | | | 435/13 |
| 2007/0235329 A1* | 10/2007 | Harding | G01N 27/26 |
| | | | 204/403.01 |
| 2008/0063566 A1 | 3/2008 | Matsumoto | |
| 2008/0124749 A1* | 5/2008 | Farnam | G01N 33/523 |
| | | | 435/13 |
| 2008/0294029 A1 | 11/2008 | Piveteau et al. | |
| 2011/0039285 A1 | 2/2011 | Sadaba Champetier De Ribes et al. | |
| 2011/0104725 A1* | 5/2011 | Pamula | B01F 13/0076 |
| | | | 435/7.92 |
| 2013/0074614 A1 | 3/2013 | Holmes et al. | |
| 2013/0118899 A1 | 5/2013 | Chen | |
| 2013/0171736 A1 | 7/2013 | Young et al. | |
| 2014/0014509 A1 | 1/2014 | Yan et al. | |
| 2014/0014533 A1 | 1/2014 | Yan et al. | |
| 2014/0065715 A1 | 3/2014 | Shin et al. | |
| 2014/0326037 A1* | 11/2014 | Fukuda | G01N 27/3273 |
| | | | 73/1.73 |
| 2015/0140671 A1 | 5/2015 | Zhang | |
| 2018/0003614 A1 | 1/2018 | Sait | |

FOREIGN PATENT DOCUMENTS

| | | |
|---|---|---|
| WO | WO-2014104807 A1 | 7/2014 |
| WO | WO-2014178827 A1 | 11/2014 |
| WO | WO-2015040441 A1 | 3/2015 |
| WO | WO-2015102726 A2 | 7/2015 |
| WO | WO-2016122707 | 8/2016 |

OTHER PUBLICATIONS

Cora Med Technologies, "Coagulation Resonance Analysis," Copyright 2015, 2 p. (Web Page) <http://www.coramedtech.com/index.php/coratech>.

PLOS One, "Real-Time Electrical Impedimetric Monitoring of Blood Coagulation Process under Temperature and Hematocrit Variations Conducted in a Microfluidic Chip," Oct. 7, 2013, 8 p.

Agilent Technologies User's Guide vol. 1, Agilent 4155B Semiconductor Parameter Analyzer, Agilent 4156B Precision Semiconductor Parameter Analyzer, Agilent Part No. 04156-90100, May 2000, Japan.

Punter-Villagrasa et al, An Instantaneous Low-cost Point-of-care Anemia Detection Device, (Research Paper), Feb. 16, 2015.

* cited by examiner

BLOOD CHARACTERISTIC MEASUREMENT

BACKGROUND

Various sensing devices are currently available for sensing different attributes of fluid, such as blood. In some cases, a microfluidic device is used to analyze a fluid sample.

BRIEF DESCRIPTION OF THE DRAWINGS

The drawings are provided to illustrate various examples of the subject matter described herein in this disclosure (hereinafter "herein" for short, unless explicitly stated otherwise) related to methods and devices, particularly those employed to analyze a blood sample, and are not intended to limit the scope of the subject matter. The drawings are not necessarily to scale.

FIG. 2A shows a "flow-based" design and FIG. 2B shows a "cavity-based" design.

FIG. 6A shows a "flow-based" design and FIG. 6B shows a "cavity-based" design.

DETAILED DESCRIPTION

Figure 1:
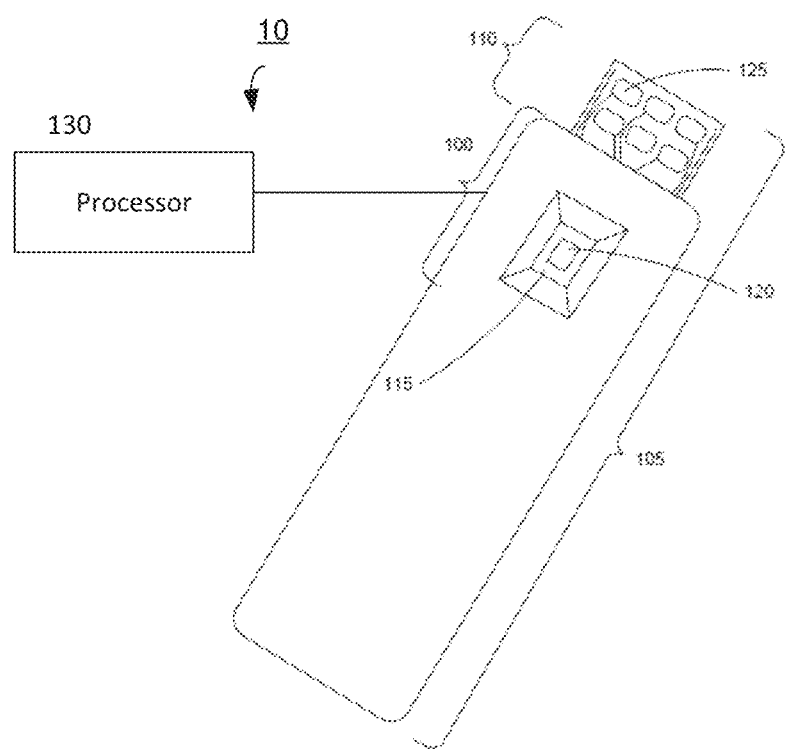
FIG. 1 provides a schematic showing an example device described herein.

Medical devices and medical testing may be used to diagnose, identify, monitor, or otherwise determine health related information. As one example, blood coagulation screening tests, such as Prothrombin Time ("PT"), Activated Partial Thromboplastin Time ("APTT"), Activated Coagulation Time ("ACT"), fibrinogen content ("FIB"), and Thrombin Time ("TT") may be performed by clinical laboratories, health practitioners, and the like. Each of these tests relates to a type of blood coagulation characteristic under a certain condition.

Clinicians may use these tests for various purposes, such as to monitor anticoagulant therapy, to screen for a single factor deficiency, to screen for multiple factor deficiencies and/or to screen for specific or non-specific inhibitors. As one example, unfractionated heparin therapy is widely used as a treatment for thromboembolic (obstructive blood clots) disorders. In some cases, heparin therapy, or the amount of heparin administered, is determined based on the result of the APTT or ACT tests. However, there are many pre-analytical and analytical variables that can affect the PT, APTT, ACT, FIB, or TT measurements, often giving dramatically different measurements from one test device or laboratory to another. This can produce a variance in the amount of a drug (e.g., heparin) or other therapy administered to the patient. Among the blood testing methods available, to date most efforts have focused on the coagulation process itself, particularly on only one time point instead of a duration of time. Even the few efforts that have performed measurement over a period of time, very little, if at all, attention has been paid to the behavior of the blood sample prior to coagulation. It has been suggested that the process leading to coagulation may provide important insight into the characteristic of the blood sample, and in turn the subject from whom the blood is obtained.

In view of the aforementioned challenges related to biological fluid sample analysis, the Inventors have recognized and appreciated the advantages of a device and a method of analyzing a blood sample as described herein. Following below are more detailed descriptions of various examples related to a method and device, particularly those that take into account both pre-coagulation and coagulation of the blood sample. The various examples described herein may be implemented in any of numerous ways.

Provided in one aspect of the examples is a method, comprising: applying an electrical potential difference over a blood sample in a testing cassette of a microfluidic device, the cassette comprising a microfluidic channel through which the blood sample flows; measuring, over a duration of time, an electrical signal passing through the blood sample as the blood sample flows from a first end and coagulates at a second end of the microfluidic channel to obtain a measurement function as a function of time; and correlating the measurement function to a characteristic of the blood sample.

Provided in another aspect of the examples is a method, comprising: applying an electrical potential difference over a blood sample in a testing cassette of a microfluidic device, the cassette comprising a microfluidic channel through which the blood sample flows; measuring, over a duration of time, an electrical signal passing through the blood sample as the blood sample flows from a first end and coagulates at a second end of the microfluidic channel to obtain a measurement function as a function of time; determining a first property and second property of the measurement function before and during coagulation, respectively; and correlating at least one of the first property and second property to a characteristic of the blood sample.

Provided in another aspect of the examples is a non-transitory machine-readable medium stored thereon instructions, which when executed, cause at least one machine to: apply an electrical potential difference over a blood sample in a testing cassette of a microfluidic device, the cassette comprising a microfluidic channel through which the blood sample flows; measure, over a duration of time, an electrical signal passing through the blood sample as the blood sample flows from a first end and coagulates at a second end of the microfluidic channel to obtain a measurement function as a function of time; and correlate the measurement function to a characteristic of the blood sample.

Provided in one aspect of the examples is a device, comprising: a testing cassette comprising: a microfluidic channel connecting an input port at a first end to at least one sensor area at a second end, the channel is to allow a blood sample to flow from the input port to the at least one sensor area; at least two electrodes; and a micro-fabricated integrated sensor, wherein when an electrical potential difference is applied over the blood sample, the sensor is to measure, over a duration of time, an electrical signal passing through the blood sample as the blood sample flows from the input port to the at least one sensor area and begin to coagulate, thereby obtaining a measurement function as a function of time; and a processor to correlate the measurement function to a characteristic of the blood sample.

Provided in another aspect of the examples is a device, comprising: a testing cassette comprising: a microfluidic channel connecting an input port at a first end to two sensor areas on opposite sides of the input port such that after the blood sample enters the channel through the input port, the sample is to flow branching out to two pathways in opposite directions in the channel to the two sensor areas; a first electrode located at the input port and a second electrode is located at each of the two sensor areas; and a micro-fabricated integrated sensor, wherein when an electrical potential difference is applied over the blood sample, the sensor is to measure, over a duration of time, an electrical signal passing through the blood sample as the blood sample flows from the input port to the sensor areas and begin to coagulate, thereby obtaining a measurement function as a function of time; and a processor to: determine a first property and second property of the measurement function before and during coagulation, respectively; and correlate at least one of the first property and second property to a characteristic of the blood sample.

Provided in another aspect of the examples is a device, comprising: a testing cassette comprising: a microfluidic channel connecting an input port at a first end an array of multiple sensor areas spanning in a first direction perpendicular to flow of the blood sample in the channel; and at least three electrodes laying along the first direction and intersecting the circumference of each of the multiple sensor areas in three different sets of locations; and a micro-fabricated integrated sensor, wherein when an electrical potential difference is applied over the blood sample, the sensor is to measure, over a duration of time, an electrical signal passing through the blood sample as the blood sample flows from the input port to the at least one sensor area to fill the channel and begin to coagulate, thereby obtaining a measurement function as a function of time; and a processor to: determine a first property and second property of the measurement function before and during coagulation, respectively; and correlate at least one of the first property and second property to a characteristic of the blood sample.

To the extent applicable, the terms "first," "second," "third," etc. herein are merely employed to show the respective objects described by these terms as separate entities and are not meant to connote a sense of chronological order, unless stated explicitly otherwise herein.

The term "fluid" is meant to be understood broadly as any substance that continually deforms (flows) under an applied shear stress. In one example, a fluid includes an analyte (e.g., sample to be analyzed). In another example, a fluid includes a reagent or reactant. In another example, a fluid includes an analyte and a reagent or reactant. In another example, a fluid includes an analyte, a reagent or reactant, among others. In one example, the fluid comprises, or is, blood. The blood may be from subjects that are any animals, such mammals. The blood sample may be obtained directly from a subject for the testing described herein or processed after being obtained from the subject before testing. The blood sample may be obtained from the subject via any suitable methods. For example, the sample may be obtained from the capillaries (e.g., by finger pricking).

The term "reagent" herein is meant to be understood as a substance or compound that is added to a system in order to bring about a chemical reaction, or added to see if a reaction occurs. A reactant is meant to be understood as a substance that is consumed in the course of a chemical reaction.

The term "a number of" or similar language is meant to be understood broadly as any positive number including 1 to infinity.

The indefinite articles "a" and "an," as used herein in this disclosure, including the claims, unless clearly indicated to the contrary, should be understood to mean "at least one." Any ranges cited herein are inclusive.

The terms "substantially" and "about" used throughout this Specification are used to describe and account for small fluctuations. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

FIG. 1 shows a diagram of an example device described herein. The device 10 comprises a testing cassette 105 with a microfluidic diagnostic chip ("MDC") 100, as well as a processor 130 for analyzing an analyte according to one example described herein. The microfluidic diagnostic chip may comprise any suitable material have any suitable function. In one example, the MDC is a micro-fabricated integrated sensor.

In the example shown in FIG. 1, the MDC 100 is part of the cassette 105. The cassette 105 further includes an electronic device interface 110 electrically coupled to the MDC 100. The interface 110 may allow the MDC 100 to receive instructions and power from an external source such as a computing device. In this example, the MDC 100 is the part of the cassette 105 that receives a fluid including an analyte while the cassette 105 and electronic device interface 110 provide the physical body to house the MDC and the power and logic to operate the MDC, respectively. However, other configurations are also possible.

The cassette 105 may serve as a housing into which the MDC 100 and electronic device interface 110 are housed and protected from contamination and damage. The cassette 105 may also serve as a structure onto which a user may apply pressure in order to connect the electronic device interface 110 to an electronic device, for example directly to a computing device or to a connector that can be attached to a computing device.

The electronic device interface 110 may include any number of electrical contact points 125 that may interface with an input/output port of an electronic device. In one example, the electronic device interface 110 is a universal serial bus (USB) interface capable of electrically coupling to a USB port in an electronic device. In other examples, the electrical contact points 125 of the electronic device interface 110 may fit into a PCI bus, a PCIE bus, a SAS bus, and a SATA bus, among others. In one example, the electronic device interface 110 may include electrical contact points 125 that interface with a specialized port in a specialized computing device. The other end of the contacts of the electrical contact points in the testing cassettes may comprise at least two electrodes (not shown). The number of the electrodes in the testing cassette may be of any value—e.g., at least three, four, five, or more.

The MDC 100 may include a feed tray 115 into which a fluid including an analyte is placed. The feed tray 115 directs the fluid into a fluidic slot 120 of the MDC 100. The fluidic slot 120 may serve as an input port of the testing cassette. During operation, the fluid is placed in the feed tray 115 and passed into the input port 120. When the fluid is in the input port 120 the MDC 100 receives electrical power from an electrical device via the electronic device interface 110. The input port may comprise any suitable material. For example, the input port may comprise silicon. In one example, after the sample enters the microfluidic channel through the input port, the sample flows to at least one sensor area, wherein at least one electrode is located, and upon filling the at least the sensor area, the coagulation may begin.

The MDC 100 may further include a number of sensors located in a number of microfluidic channels defined in the MDC 100. The sensor may be a micro-fabricated integrated sensor. In one example, the sensors are impedance sensors capable of measuring an impedance value of a fluid including an analyte as the fluid is passed over the sensor. In one example, these sensors may measure an electrical signal of the fluid sample (e.g., blood) over time. The electrical signal may be, for example, impedance, voltage, etc., or combinations thereof. In one example, the sensors may measure the electrical signal of the sample at any time, for any number of intervals, and over any length of time based on the analysis to be completed. In one example where a microfluidic pump is used to pump the fluid through the MDC 100, the sensors may measure the impedance of the fluid while the pump is not pumping.

Figure 2:
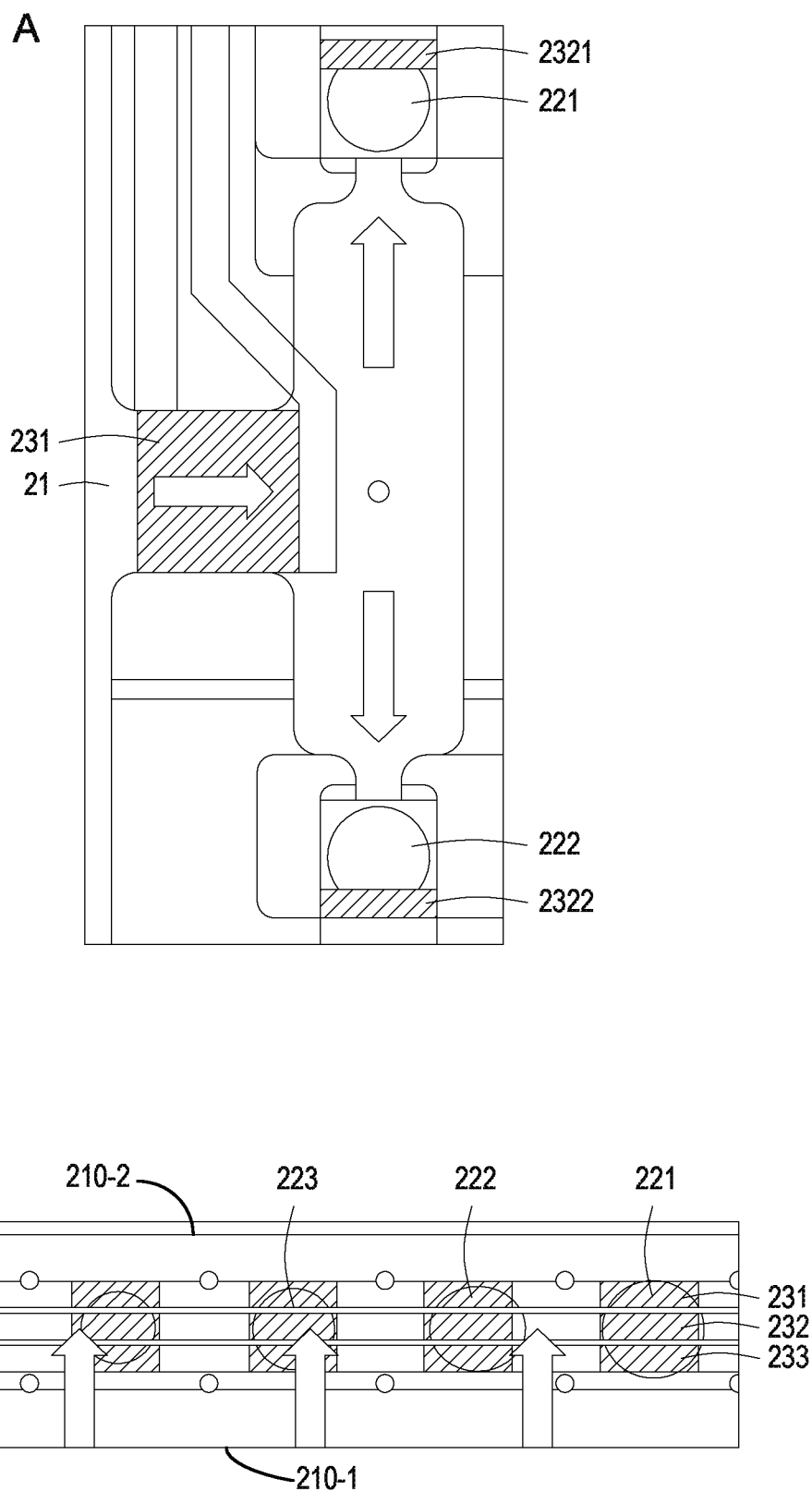
FIGS. 2A and 2B are schematic diagrams showing two examples of the testing cassettes described herein.

FIG. 2A shows one example of the device described herein, particularly focusing on a specific testing cassette configuration. It is noted that FIG. 2A focuses only on the testing cassette portion of the device described herein, and the remaining portion of the device may be as shown in FIG. 1. In some instances, this configuration may be considered as "flow-based." In this example, the testing cassette comprises two sensor areas 221, 222 on opposite sides of the input port 21 such that after the blood sample enters the channel through the input port, the sample is to flow branching out to two pathways in opposite directions in the channel to the two sensor areas—the flow direction of the blood sample is shown by the arrows in the figure. In this example, the testing cassette comprises at least two electrodes, of which a first electrode 231 is located at the input port 21 and a second electrode 2321, 2322 is located at each of the two sensor areas 221, 222, respectively. In a flow-based configuration, as the blood sample flows from the input port to the sensor areas, the sample may travel over the electrodes. As cells travel across the electrodes, the system may measure a flow signal until the chamber has been filled and coagulation begins.

FIG. 2B shows another example of the device described herein, particularly focusing on a specific testing cassette configuration. FIG. 2B focus only on the testing cassette portion of the device described herein, and the remaining portion of the device may be as shown in FIG. 1. In some instances, this configuration may be considered as "cavity-based." In this example, the testing cassettes comprises an array of multiple sensor areas 221, 222, 223, etc., spanning in a first direction perpendicular to flow of the blood sample in the channel (flow direction shown 1w arrows). In this example, the cassette has at least three electrodes 231, 232, 233 laying along this first direction and intersecting the circumference of each of the multiple sensor areas in three different sets of locations, in a cavity-based configuration, the electrodes may be located under the array of multiple sensor areas. Blood sample may flow from the input port (at the bottom of the figure but not show) to the sensor areas and the blood sample with the different constituents thereof pack over the electrodes. Fluid flows from the first end 210-1 of the channel to the second end 210-2 of the channel as shown by the arrows. It is noted that the two configures as shown in FIGS. 2A and 2B are just illustrative examples, and other configurations may also be possible.

The sensor areas described herein may have any suitable surface area values. For example, each sensor area can be between about 500 $\mu m^2$ and about 5000 $\mu m^2$—e.g., between about 100 $\mu m^2$ and about 4000 $\mu m^2$, between about 500 $\mu m^2$ and about 3000 $\mu m^2$, between about 1000 $\mu m^2$ and about 2000 $\mu m^2$, etc. Other values are possible. The sensor areas of the flow-based configuration may be larger, smaller, or the same as those of the cavity-based configuration.

The sensor in the microfluidic channels may be employed to make any suitable measurements, depending on the application. For example, when an electrical potential difference is applied over the blood sample, the sensor may be employed to measure, over a duration of time, an electrical signal passing through the blood sample as the blood sample flows from the input port to the at least one sensor area and begin to coagulate. The measurement may be continuous until the coagulation is completed. In the examples described herein, the completion of the coagulation is deemed to be when a fibrin gel has complemented form over the electrode and the blood sample is no longer in a fluid form. The result of the measurement may be a measurement function as a function of time, such as the schematic shown in FIG. 3. In one example, the blood sample fills the channel before coagulation begins.

The processor of the device, such as process 130 shown in FIG. 1, may be in the interior of the device (e.g., within a housing) or it may be detachably connected to the device, such as through a wire. The processor may be, for example, a computer. It is noted that when any aspect of an example described herein is implemented at least in part in software, the software code can be executed on any suitable processor or collection of processors, whether provided in a single computer or distributed among multiple computers.

The processor may be employed to perform any suitable functions. For example, the processor to correlate the measurement function to a characteristic of the blood sample. In one example, the process may be employed to determine a first property and second property of the measurement function before and during coagulation, respectively, and correlate at least one of the first property and second property to a characteristic of the blood sample. The property may refer to any aspect of the measurement function, such as magnitude, slopes, number of local maxima and/or minima, shape, etc. In one example, the property refers to any suitable parameter that may be extracted from the measurement function. In one example, the properties of both pre-coagulation and during coagulation are employed for the correlation.

The characteristic may refer to any parameter of interest. For example, the characteristic may be hematocrit; health, size, or shape of red blood cells; or combinations thereof. In one example, the characteristic includes at least one of: at least one of a flow rate and flow volume of red blood cells; arrival of platelets; at least one of activation, adhesion, aggregation, reaction, and plug formation of platelets; conversion of prothrombin to thrombin and fibrinogen to fibrin; and formation of a stable fibrin polymer (gel).

The testing cassette may be detachable from the device. The device may be a microfluidic device that is a part of a mobile apparatus, such as a handheld mobile device. For example, the device may be a mobile phone, a tablet, a phablet, etc.

The microfluidic device, including the sensor, microfluidic channel, reservoir, etc. described above, may be used to perform measurements and/or analyses on a biological fluid sample, such as a blood sample. Using the characteristic of the sample, based on the result of the correlated measurement function, a condition of the sample, and in turn the subject from which the sample is obtained, may be determined. As a result, based on the result of the analysis, appropriate treatment may be applied to the subject (that provides the sample) in need thereof.

The device, using for example the processor, may send the result of the analysis to a storage device and store the result therein. The result may refer to the measurement raw data and/or the correlation performed with respect to the characteristic of the blood. The storage may be located in the device or electrically connected to the device (e.g., via a wire). The device may be remote to the device, such as a storage in a remote location. For example, the device may store the result in the "cloud." It is noted that during the analysis, the processor may call upon the stored data from the storage device and compare the data as measured with the data previously obtained and stored.

The microfluidic device in the testing cassette may include a number of microfluidic channels including at least one sensor and a number of pumps to pump a fluid though the number of microfluidic channels wherein presence of the fluid on the sensor detects changes in the chemical characteristics of the fluid.

As explained above, the MDC is part of the cassette. The cassette may further include an electronic device interface electrically coupled to the MDC. The interface may allow the MDC to receive instructions and power from an external source such as a computing device. In one example, the MDC is the part of the cassette that receives a fluid including an analyte while the cassette and electronic device interface provide the physical body to house the MDC and the power and logic to operate the MDC respectively.

In some examples, the device may further comprise a transport mechanism. The mechanism may operating using at least one of a capillary pump, a thermal inkjet pump, and a pneumatic pump. In one example, the mechanism may employ kinetic energy. For example, the cassette may include a number of resistors that serve as both microfluidic heaters and microfluidic pumps depending on the amount and/or the duration of the voltage applied to the resistor. The MDC may further include a bore that serves as a hole through which an amount of fluid in the MDC is ejected out of a microfluidic channel defined in the MDC. During operation of the MDC, a number of fluids may be introduced into a fluidic slot. The fluid may then flow, using a number of inlets, into a number of microfluidic channels. The flow of the fluid into these microfluidic channels is initially accomplished using capillary action and subsequently through the use of a resistor as a microfluidic pump (pump resistor). In some examples, the fluid may be mixed, reacted with another fluid, heated, pumped, and recirculated through the fluidic slot and microfluidic channels, discharged from the MDC, or combinations thereof.

The resistors may be thin film resistors. The thin film resistor may comprise tantalum or tantalum aluminum, platinum, gold, silicon carbide, silicon nitride, tungsten, or combinations thereof. In one example, the thickness of the resistor may be approximately 500 angstroms to 5000 angstroms. The resistor may be encapsulated with a passive film which is then encapsulated with a cavitation film. In one example, the passive film may comprise SiC or SiN and may be approximately 500-2000 angstroms thick. In another example, the cavitation film comprises tantalum or platinum and may be approximately 500-2000 angstroms thick.

In some examples, the testing cassette may comprise a discharge reservoir (not shown). A discharge reservoir may comprise a cavity or chamber within a body arranged to receive fluid discharged from the MDC. In one example, the discharge reservoir has a minimum volume of 10 µL. Discharge reservoir contains fluid that has been passed through chip and that has been processed or tested. In one example, the discharge reservoir extends below microfluidic chip on an opposite side of microfluidic chip as sample input port such that microfluidic chip is sandwiched between sample input port and discharge reservoir. Discharge reservoir receives processed or tested fluid such that the same fluid is not tested multiple times. In one example, the discharge reservoir is completely contained within body and is inaccessible (but through the destruction of body such as by cutting, drilling or other permanent structures are breaking of body), locking the processed or tested fluid within body for storage or subsequent sanitary disposal along with disposal of cassette. In another example, the discharge reservoir is accessible through a door or septum, allowing processed or tested fluid to be withdrawn from reservoir further analysis of the tested fluid, for storage of the tested fluid in a separate container or for emptying of reservoir to facilitate continued use of cassette.

The testing cassette may comprise additional sub-components. The testing cassette may also comprise a removable packaging completely enclosing a body of the testing cassette body. For example, a fluid delivery component that may promote mixing of the sample with another reagent (e.g., buffer solution) prior to the sample-reagent mixture reaches the sensor area may be employed. The cassette may include additional components that would facilitate automation of sample preparation prior to the sample reaches the sensor areas. These additional components may comprise any suitable materials. In one example, these components comprise a plastic. Other additional suitable sub-components may be employed.

The devices described herein may provide relatively high sensitivity while using a relatively small volume for measurement. For example, the volume of the blood sample used for the measurement may be less than or equal to about 10 microliters—e.g., less than or equal to about 1 microliter, about 800 pico-liters, about 600 pico-liters, about 400 pico-liters, about 200 pico-liters, about 100 pico-liters, about 80 pico-liters, about 60 pico-liters, about 40 pico-liters, about 20 pico-liters, or lower. Other values are also possible.

Analysis Methods

The technology described herein may be implemented as a method, of which at least one example has been provided. The acts performed as part of the method may be ordered in any suitable way. Accordingly, examples may be constructed in which acts are performed in an order different than illustrated, which may include performing some acts simultaneously, even though shown as sequential acts in illustrative examples.

Figure 4:
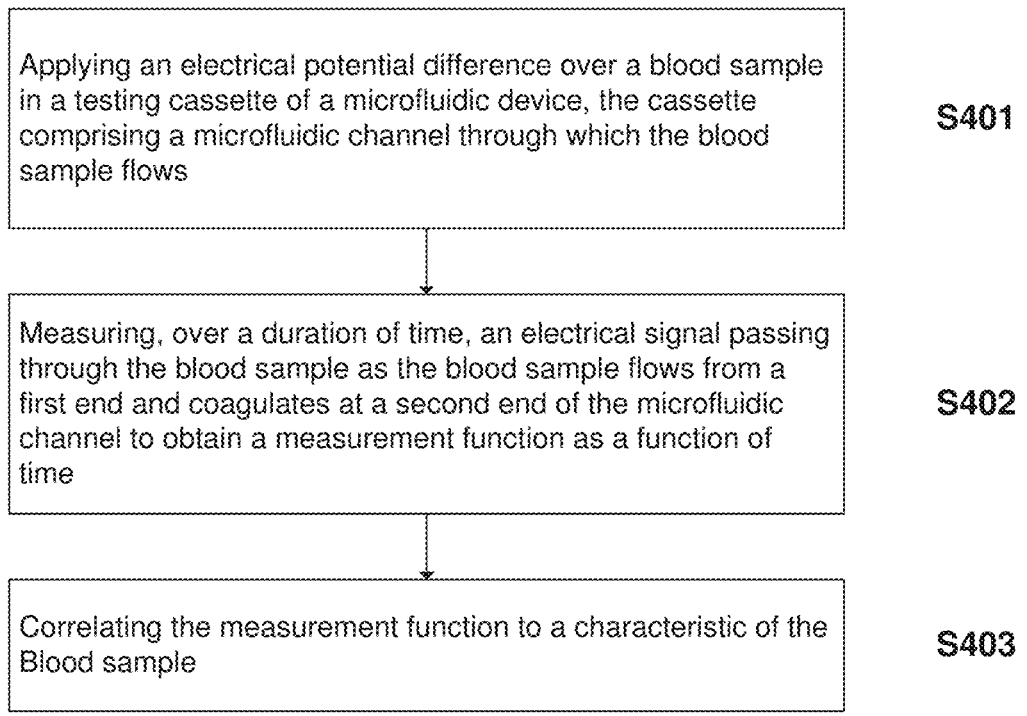
FIG. 4 provides a flowchart illustrating an example method described herein.

FIG. 4 provides a flowchart illustrating such an example. As shown in the figure, the method may comprise applying an electrical potential difference over a blood sample in a testing cassette of a microfluidic device, the cassette comprising a microfluidic channel through which the blood sample flows (S401). The method may comprise measuring, over a duration of time, an electrical signal passing through the blood sample as the blood sample flows from a first end and coagulates at a second end of the microfluidic channel to obtain a measurement function as a function of time (S402). Also, the method may comprise correlating the measurement function to a characteristic of the blood (S403).

Figure 5:
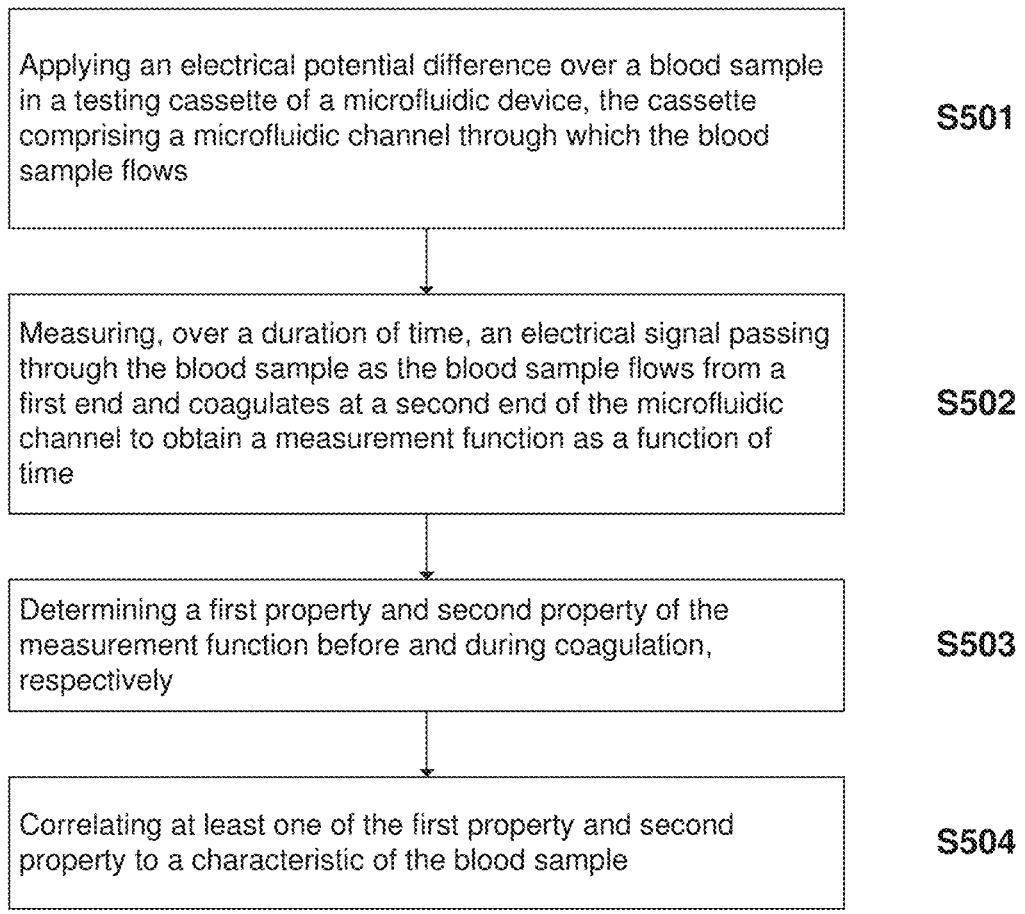
FIG. 5 provides a flowchart illustrating another example method described herein.

FIG. 5 provides a flowchart illustrating another example of such a method. As shown in the figure, the method may comprise applying an electrical potential difference over a blood sample in a testing cassette of a microfluidic device, the cassette comprising a microfluidic channel through which the blood sample flows (S501). The method may comprise measuring, over a duration of time, an electrical signal passing through the blood sample as the blood sample flows from a first end and coagulates at a second end of the microfluidic channel to obtain a measurement function as a function of time (S502). The method may comprise determining a first property and second property of the measurement function before and during coagulation, respectively (S503). The method may additionally comprise correlating at least one of the first property and second property to a characteristic of the blood sample (S504).

The testing cassette and device may be any of those described herein. For example, the testing cassette may comprise an input port in fluid communication with a microfluidic reservoir, the input port to receive the discharged fluid sample from the output port. The testing cassette may also comprise a micro-fabricated integrated sensor within a microfluidic channel extending from the microfluidic reservoir.

The analysis may refer to any type of analysis that may translate the results measured by the testing cassette into meaningful data. The analysis may involve using algorithm and at least one processor to perform any number of calculations and/or comparison. In some examples, the analysis result may be employed to further provide treatment to the subject (from which the sample is obtained) in need thereof.

The methods described herein may include additional processes to those already described above. For example, the method may determining a property of the measurement function and correlating the determined property to the characteristic. The property may be any of those already described above. Moreover, the method may further include outputting the result of the analysis, including at least the measurements, the correlated measurement function, or any aspect of the analysis. The information outputted may be on a display that is a part of the device or separate from the device. For example, the device may comprise a display to display the information. For example, the device may send the information to a display that is connected to the device by wire or by wireless transmission and display the desired information. In one example, the information is displayed on a mobile device that may be the device itself or be separate from the device performing the measurement and/or analysis.

As described above, the method may further include storing at least one of the measurements and the correlated measurement function in a storage device. In another example, the method includes comparing the correlated measurement function with a previously obtained and stored correlated measurement function. In another example, the method further includes determining a condition of a subject from which the blood sample is obtained using the correlated measurement function and providing the subject a treatment in need thereof. In another example, the method includes continuously outputting, using an output device, at least one of the measurement function and the determined property (or properties). As described above, the storage may be remote to the device—e.g., "cloud" with a remote storage device. In another example, the processor to perform the analysis and calculation is also remote to the measurement device—e.g., "cloud computing."

Various examples described herein may be embodied at least in part as a non-transitory machine-readable storage medium (or multiple machine-readable storage media)—e.g., a computer memory, a floppy disc, compact disc, optical disc, magnetic tape, flash memory, circuit configuration in Field Programmable Gate Arrays or another semiconductor device, or another tangible computer storage medium or non-transitory medium) encoded with at least one machine-readable instructions that, when executed on at least one machine (e.g., a computer or another type of processor), cause at least one machine to perform methods that implement the various examples of the technology discussed herein. The computer readable medium or media can be transportable, such that the program or programs stored thereon can be loaded onto at least one computer or other processor to implement the various examples described herein.

The term "machine-readable instruction" are employed herein in a generic sense to refer to any type of machine code or set of machine-executable instructions that may be employed to cause a machine (e.g., a computer or another type of processor) to implement the various examples described herein. The machine-readable instructions may include, but not limited to, a software or a program. The machine may refer to a computer or another type of processor. Additionally, when executed to perform the methods described herein, the machine-readable instructions need not reside on a single machine, but may be distributed in a modular fashion amongst a number of different machines to implement the various examples described herein.

Machine-executable instructions may be in many forms, such as program modules, executed by at least one machine (e.g., a computer or another type of processor). Generally, program modules include routines, programs, objects, components, data structures, etc. that perform particular tasks or implement particular abstract data types. Typically, the functionality of the program modules may be combined or distributed as desired in various examples.

For example, provided herein is a non-transitory machine-readable medium stored thereon instructions, which when executed, cause at least one machine to perform any of the processes described herein. In one example, the analysis method include: applying an electrical potential difference over a blood sample in a testing cassette of a microfluidic device, the cassette comprising a microfluidic channel through which the blood sample flows. The method may also include measuring, over a duration of time, an electrical signal passing through the blood sample as the blood sample flows from a first end and coagulates at a second end of the microfluidic channel to obtain a measurement function as a function of time. The method may also include correlating the measurement function to a characteristic of the blood sample.

Non-Limiting Working Example

Materials and Method

Figure 6:
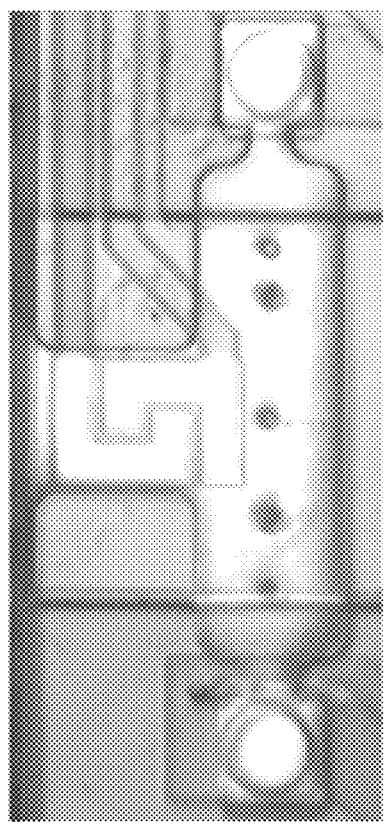
FIGS. 6A and 6B are optical images showing two examples of the testing cassettes described herein.
Figure 6:
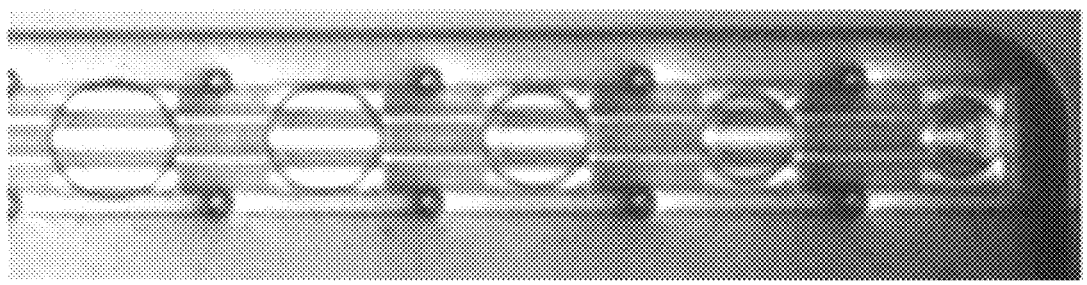

In this example, two configurations of testing cassettes were investigated: flow-based (as shown in FIG. 6A) and cavity-based (as shown in FIG. 6B). As shown in FIG. 6A, the flow-based design has electrodes that are separated from the sensor areas. In this design, blood sample flows from the silicon slot to the sensor areas and travel over the electrodes. As cells travel across the electrodes, the system measures a flow signal until the chamber has been filled and coagulation begins. As shown in FIG. 6B, the cavity-based design has the electrodes located under the sensor areas. In this design, blood sample flows from the silicon slot to the sensor areas and red blood cells pack over the electrodes, giving a distinct packing signal prior to the start of coagulation.

All data sets presented were collected using the mobile system, which included a tablet and a cassette reader. Prior to the commencement of the test, the MDC's were inserted and primed using HT-glucose buffer solution. Voltage measurements were taken to ensure the buffer solution wet the entire microfluidics of the chip. The test duration varied depending on the chip design and type of sample being tested.

Results and Discussion

Figure 3:
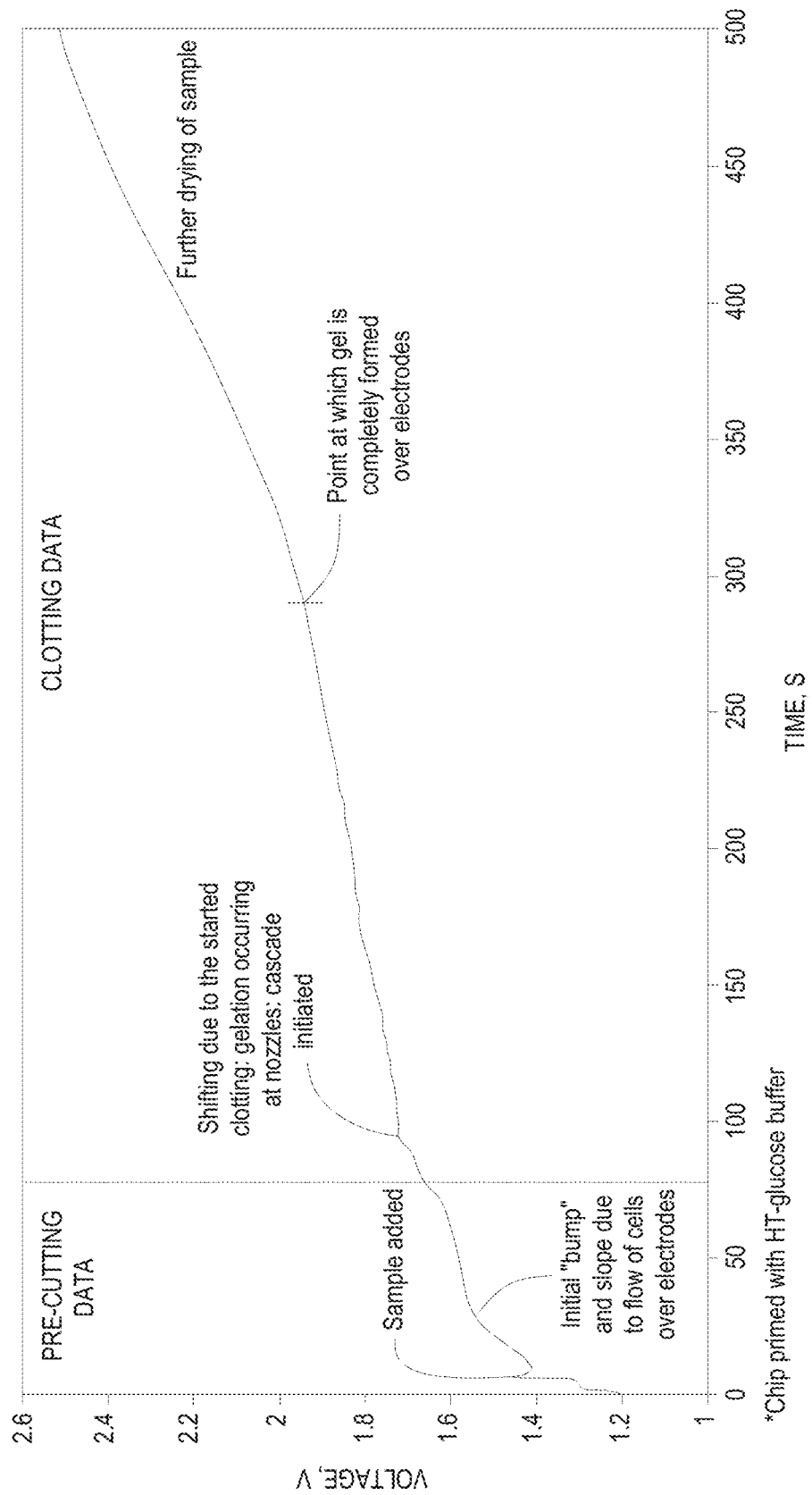
FIG. 3 shows an example of the voltage vs. time data collected using the design as shown in FIG. 6A.

FIG. 3 is an example of the voltage vs. time data collected using the design as shown in FIG. 6A. The pre-coagulation data include a signal related to the flow of red blood cells. The coagulation data includes the initiation of the coagulation cascade as well as the conversion of fibrinogen to fibrin. Each test includes both pre-coagulation data related to either the flow or packing of red blood cells, as well as coagulation data related to the initiation of the coagulation cascade and conversion of fibrinogen to fibrin. It is believed that pre-coagulation data provide information related to red blood cells, such as hematocrit, hemoglobin, and flow rate (which can in turn be correlated to shape and health). It is also believed that coagulation data provide information about a patient's coagulation capabilities, which will be correlated to PT-INR or APTT depending on the reagent used inside the chip. In this Example, the sample's coagulation time is the point at which a gel has completely formed over the electrodes.

Figure 7A:
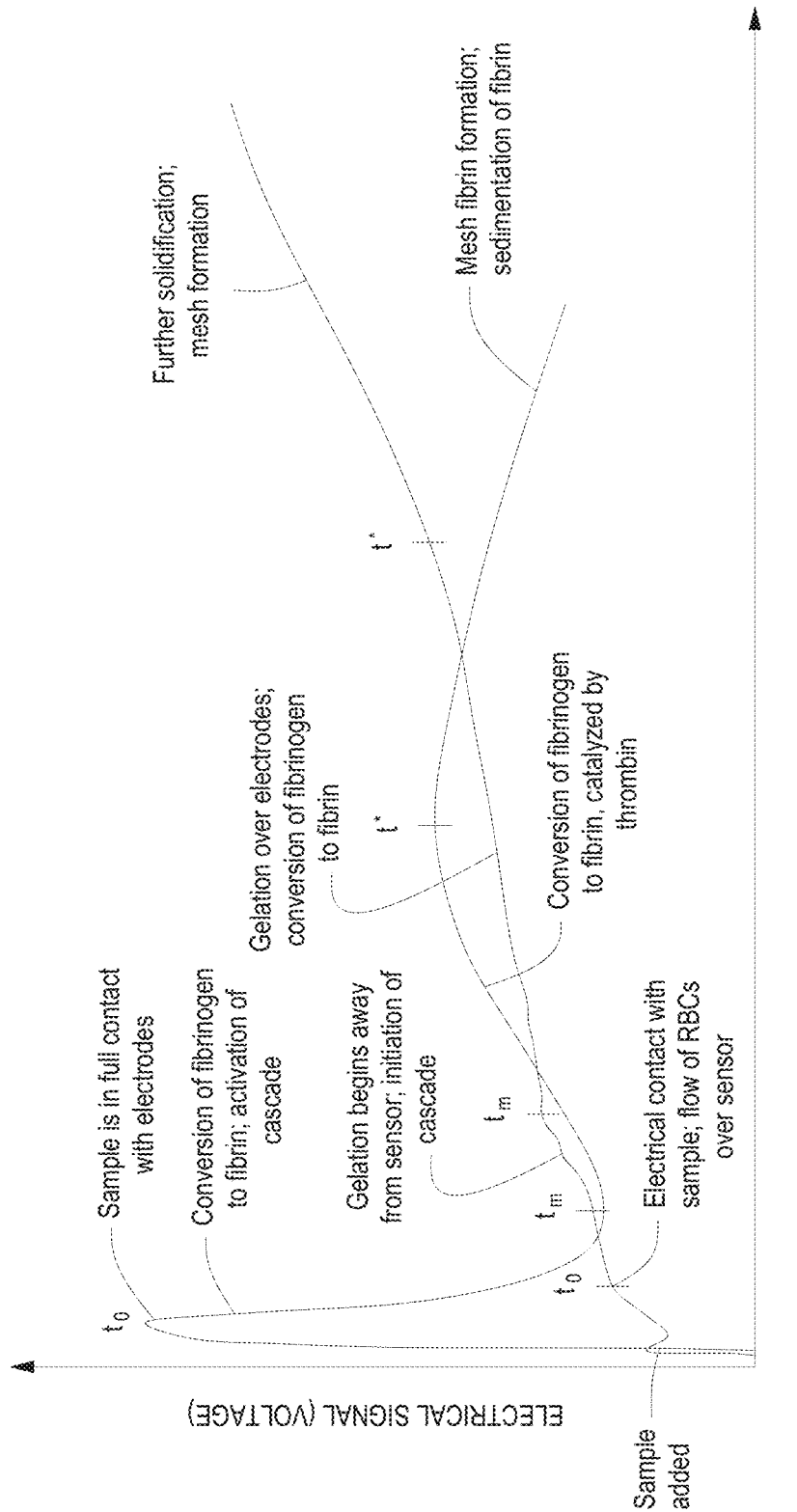
FIGS. 7A and 7B illustrate, in one example, the contrast between taking into account (1) both pre-coagulation and coagulation data and (2) only coagulation data in the flow-based design (FIG. 7A) and in the cavity-based design (FIG. 7B).
Figure 7B:
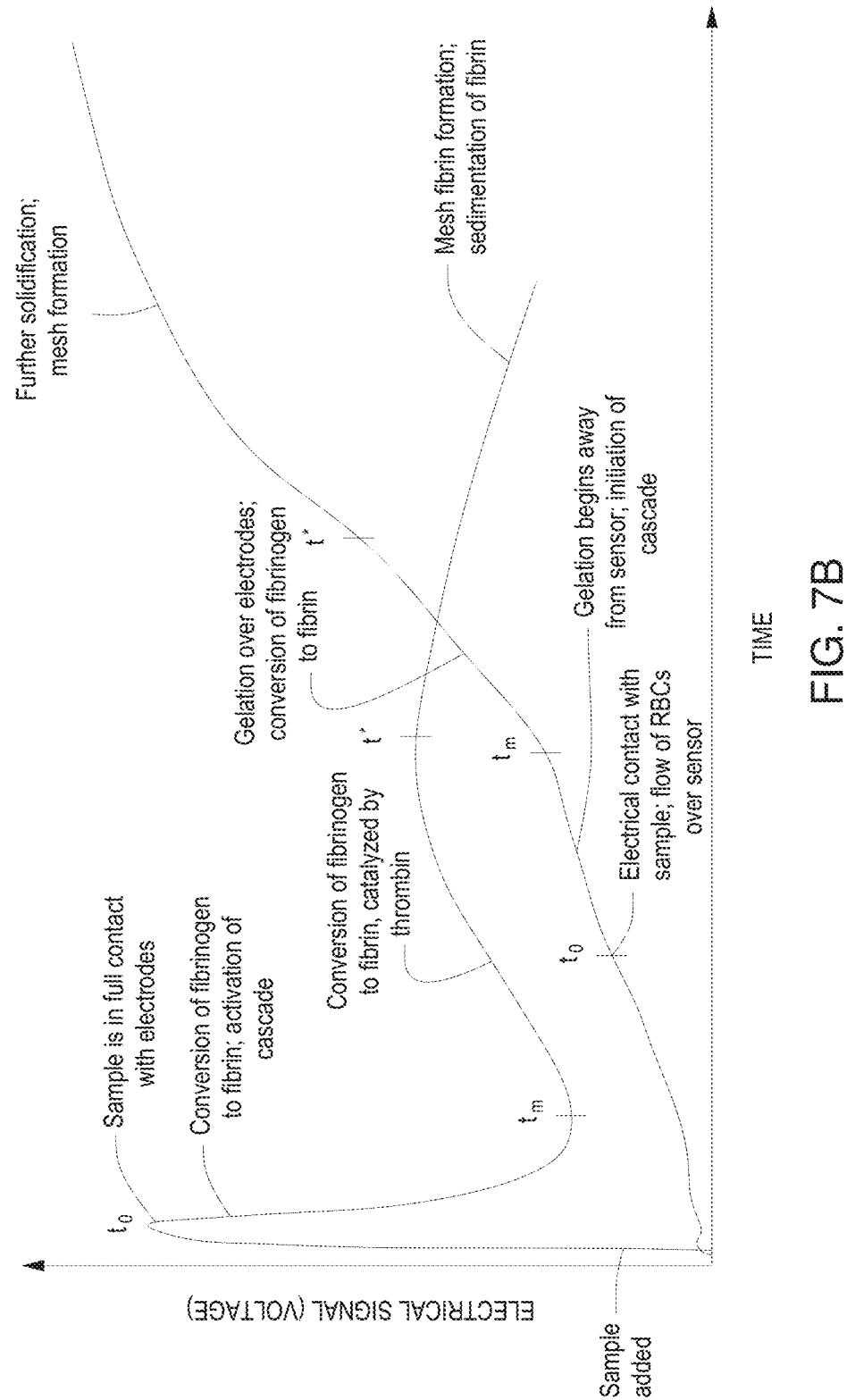

FIGS. 7A and 7B illustrate the contrast between taking into account (1) both pre-coagulation and coagulation data and (2) only coagulation data in the flow-based design (FIG. 7A) and in the cavity-based design (FIG. 7B). In each of FIGS. 7A and 7B, "Curve 1" illustrates a curve obtained when the measurement only from the beginning of the coagulation, whereas "Curve 2" shows the data curve for which measurement begins when the blood sample enters through the input port and flows to the electrode to begin coagulation. The different events of the blood sample for each scenario is labeled in the two figures. It is noted that Curve 1 is a schematic representation and do not represent data actually measured in this Example.

Curve 1 shows a tall peak in the data followed by an increase to form either a very broad peak or a plateau. Voltage measurements made by the two designs of this Example both trend upward through the duration of the test.

Figure 8:
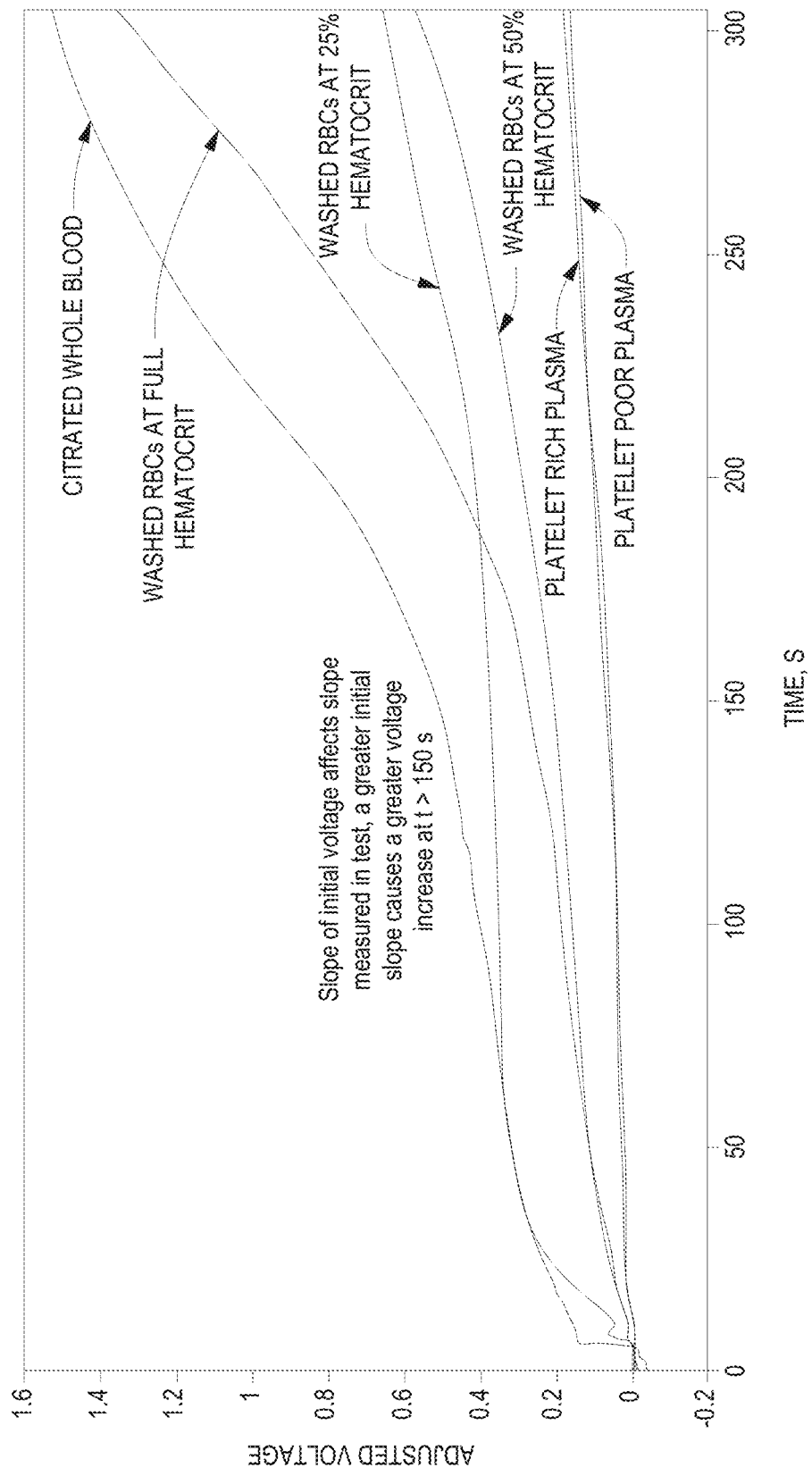
FIG. 8 provides a plot of voltage vs. time that analyzes the effect of red blood cell concentration on the signal measured in one example described herein.

FIG. 8 provides a plot of voltage vs. time that analyzes the effect of red blood cell concentration on the signal measured during the test in this Example. Red blood cell concentration appears to have an effect on the initial rise in voltage between t=5 s and t=50 s. This initial rise then affects the slope in the latter portion of the test. A greater slope in the initial rise appears to cause a greater slope at t>150 s.

In particular, FIG. 8 illustrates the effect pre-coagulation data can have on the entire test. The data include whole blood, as well as samples containing different percentages of red blood cells and was collected using a cavity-based design. The washed red blood cells samples were made by extracting red blood cells from a venous whole blood sample, washing them, and then re-suspending them in bovine serum to mimic the consistency of human whole blood. The washed red blood cell sample with full hematocrit had the same volume percentage of red blood cells as the original whole blood sample. The washed samples at 50% and 25% of hematocrit were diluted to determine if a decrease in the number of red blood cells would affect the signal measured in the system. The two plasma samples did not contain red blood cells; the difference between these two samples was the concentration of platelets present. All samples were citrated to prevent coagulation.

It was observed that red blood cell concentration appears to have an effect on the initial rise in voltage (between t=5 s and t=50 s). A greater concentration of red blood cells increases the magnitude of this initial rise (there is a greater slope at this point). The slope of this initial rise appears to affect the slope measured in the latter portion of the test. A greater slope in the initial rise appears to cause a greater slope at t>150 s. Since all these samples were anticoagulated, it can be assumed that the signals measured are due to packing of and interactions between red blood cells.

Additional Notes

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A method, comprising:
    applying an electrical potential difference over a blood sample in a testing cassette of a microfluidic device, the cassette comprising a microfluidic channel through which the blood sample flows, wherein the microfluidic channel comprises an array of at least three sensor areas, each of the at least three sensor areas comprising at least three electrodes located parallel to each other and perpendicular to a direction of flow in the microfluidic channel, wherein each sensor area comprises multiple electrodes;
    beginning as soon as the blood sample enters an input port of the testing cassette at a first end of the microfluidic channel:
        measuring an electrical signal passing through the blood sample as the blood sample flows from the first end to obtain a pre-coagulation property of a measurement function; and
        measuring an electrical signal passing through the blood sample as the blood sample coagulates at a second end of the microfluidic channel to obtain a coagulation property of the measurement function as a function of time through the multiple electrodes of the sensor areas; and
    correlating the measurement function to a characteristic of the blood sample.

2. The method of claim 1, wherein the electrical signal is at least one of voltage and impedance.

3. The method of claim 1, further comprising determining a property of the measurement function and correlating the determined property to the characteristic.

4. The method of claim 1, further comprising outputting the correlated measurement function on a mobile device.

5. The method of claim 1, further comprising storing at least one of the measurements and the correlated measurement function in a storage device.

6. The method of claim 1, further comprising comparing the correlated measurement function with a previously obtained and stored correlated measurement function.

7. The method of claim 1, further comprising comparing the correlated measurement function with a previously obtained correlated measurement function for determining a condition of a subject from which the blood sample is obtained based on the correlated measurement function.

8. The method of claim 1, wherein the characteristic includes at least one of:
   at least one of a flow rate and flow volume of red blood cells;
   arrival of platelets;
   at least one of activation, adhesion, aggregation, reaction, and plug formation of platelets;
   conversion of prothrombin to thrombin and fibrinogen to fibrin; and
   formation of a stable fibrin polymer.

9. The method of claim 1, wherein the characteristic is hematocrit, health, size, or shape of red blood cells, or combinations thereof.

10. The method of claim 1, further comprising operating a first electrode located at the input port and a second electrode located at the second end of the microfluidic channel, opposite from the input port, to begin measuring the electrical signal as soon as the blood sample enters the input port.

11. The method of claim 1, wherein the characteristic comprises flow rate of red blood cells.

12. The method of claim 1, wherein the characteristic comprises arrival or activation of platelets.

13. A method, comprising:
   introducing a blood sample through an input port of a testing cassette;
   applying an electrical potential difference over the blood sample in the testing cassette, the cassette comprising a microfluidic channel through which the blood sample flows from the input port, wherein the microfluidic channel comprises an array of at least three sensor areas, each of the at least three sensor areas comprising at least three electrodes located parallel to each other and perpendicular to a direction of flow in the microfluidic channel, wherein each sensor area comprises multiple electrodes;
   beginning as soon as the blood sample enters the input port of the testing cassette at a first end of the microfluidic channel:
      measuring an electrical signal passing through the blood sample as the blood sample flows from the first end of the microfluidic channel to obtain a pre-coagulation property of a measurement function; and
      measuring an electrical signal passing through the blood sample as the blood sample coagulates at a second end of the microfluidic channel to obtain a coagulation property of the measurement function as a function of time through the electrodes of the sensor areas;
   determining a first property and second property of the measurement function before and during coagulation, respectively; and
   correlating at least one of the first property and second property to a characteristic of the blood sample.

14. The method of claim 13, further comprising comparing the correlated measurement function with a previously obtained correlated measurement function for determining a condition of a subject from which the blood sample is obtained based on the correlated measurement function.

15. The method of claim 13, further comprising continuously outputting at least one of the measurement function and the determined first property and second property.

16. The method of claim 13, wherein both the first property and the second property are employed to correlate to the characteristic.

17. The method of claim 13, wherein the testing cassette is detachable from the microfluidic device.

18. A microfluidic device for testing a blood sample, the device comprising:
   a cassette comprising:
      an input port to receive a blood sample;
      an electrode at the input port to detect introduction of the blood sample;
      a microfluidic channel through which the blood sample flows;
      an array of at least three sensor areas within the microfluidic channel, each of the at least three sensor areas comprising at least three electrodes located parallel to each other and perpendicular to a direction of flow in the microfluidic channel, wherein each sensor area comprises multiple electrodes;
      a pump to pump the blood sample through the microfluidic channel;
      a number of impedance sensors located in the microfluidic channel; and
      an electronic device interface to connect to a computing device;
   a processor; and
   a non-transitory machine-readable medium, in communication with the processor, having instructions stored thereon which, when executed by the processor, cause the device to:
      apply an electrical potential difference over the blood sample using the electrode;
      measure an electrical signal passing through the blood sample as the blood sample flows from a first end of the microfluidic channel to obtain a pre-coagulation property of a measurement function; and
      measure an electrical signal passing through the blood sample as the blood sample coagulates at a second end of the microfluidic channel to obtain a coagulation property of the measurement function as a function of time through the multiple electrodes of the sensor areas; and
      correlate the measurement function to a characteristic of the blood sample.

19. The microfluidic device of claim 18, wherein a first sensor area and a second sensor area are on opposite sides of the input port.

20. The microfluidic device of claim 18, wherein the electronic device interface is a universal serial bus (USB) interface.

* * * * *